United States Patent [19]
Collin

[11] Patent Number: 5,876,762
[45] Date of Patent: Mar. 2, 1999

[54] PROCESS FOR OBTAINING MEDICALLY ACTIVE FRACTIONS FROM SEA CUCUMBERS

[75] Inventor: Peter Donald Collin, Sunset, Me.

[73] Assignee: Coastside Bio Resources, Stonington, Me.

[21] Appl. No.: 692,176

[22] Filed: Aug. 5, 1996

[51] Int. Cl.$^6$ .......................... A61K 35/12; A61K 35/78
[52] U.S. Cl. ...................... 424/520; 424/195.1; 424/572; 514/783; 514/822; 514/825; 514/885
[58] Field of Search .................................. 424/195.1, 520, 424/572; 514/23, 25, 54, 783, 822, 825, 885

[56] References Cited

U.S. PATENT DOCUMENTS

| 3,405,120 | 10/1968 | Kawano et al. | 260/234 |
| 4,900,815 | 2/1990 | Tanaka et al. | 536/54 |
| 5,519,010 | 5/1996 | Fan et al. | 514/54 |

FOREIGN PATENT DOCUMENTS

| 408770 | 1/1991 | European Pat. Off. . |
| 58-148825 | 9/1983 | Japan . |
| 94070085 | 9/1994 | Japan . |
| 9008784 | 8/1990 | WIPO . |
| 9009181 | 8/1990 | WIPO . |
| 9202231 | 2/1992 | WIPO . |

OTHER PUBLICATIONS

Kalyani et al., "Holothurin—A Review", Ind. J. Natl. Prod., vol. 4(2): 3–8, 1988.
Mourao et al., "Structure and Anticoagulant Activity of a Fucosylated Chondroitin Sulfate from Echinoderm", Journal of Biological Chemistry, vol. 271, No. 39, pp. 23973–23984, 1996.
Matsumura et al., "Disaggregation of Connective Tissue: Preparation of Fibrous Components from Sea Cucumber Body Wall and Calf Skin", J. Biochem., vol. 73: 155–162, 1973.
Santhakumari et al., "Antimitotic effects of Holothurin", Cytologia, vol. 53: 163–168, 1988.
Miyamoto et al., "Six Newly Identified Biologically Active Triterpenoid Glycoside Sulfates from the Sea Cucumber *Cucumaria echinata*", Liebigs. Ann. Chem., pp. 453–460, 1990.
Pettit et al., "Antineoplastic Agents XLV: Sea Cucumber Cytotoxic Saponins", Journal of Pharmaceutical Sciences, vol. 65(10): 1558–1559, 1976.
Anisimov et al., "Comparative Study of Cytotoxic Activity of Triterpene Glycosides from Marine Organisms", Toxicon, vol. 18: 221–223, 1980.
Rodriguez et al., "Holothurinosides: New Antitumor Non Sulphated Triterpenoid Glycosides From The Sea Cucumber Holothuria Forskalii", Tetrahedron, vol. 47, No. 26, pp. 4753–4762, 1991.
Sumi et al., Comp. Biochem. Physiol., B: Comp. Biochem. 102(B):163–172. Abstract Only, 1992.
Yaacob et al., Malaysian Applied Biology, 24(1):23–28. Abstract Only, 1995.
Rodriguez et al., Tetrahedron, 47/26:4753–4762. Abstract Only, 1991.
Miyamoto et al., Liebigs Ann. Chem., 5:453–460. Abstract Only, 1990.
Santhakumari et al., Cytologia(Tokyo), 53(1):163–168. Abstract Only, 1988.
Kuznetsova et al., Comp. Biochem. Physiol. C Comp. Pharmacol., 73(1):41–44. Abstract Only, 1982.
Pettit et al., J. Pharm. Sci., 65(10):1558–1559. Abstract Only, 1976.
Vieira, Ricardo P., Occurrence of a Unique Fucose–branched Chondroitin Sulfate in the Body Wall of a Sea Cucumber. *J. Biol. Chem.*, 263(34):18176–18183 (1988).
Mulloy, Barbara et al., Sulfated Fucans from Echinoderms Have a Regular Tetrasaccharide Repeating Unit Defined by Specific Patterns of Sulfation of the 0–2 and 0–4 Positions. *J. Biol. Chem.*, 269(35):22113–22123 (1994).
Vieira, Ricardo P., et al., Structure of a Fucose–branched Chondroitin Sulfate from Sea Cucumber. *J. Biol Chem.*, 266(21):13530–13536 (1991).
Eylers, John P., Ion–Dependent Viscosity of Holothurian Body Wall and Its Implications for the Functional Morphology of Echinoderms. *J. Exp. Biol.*, 99:1–8 (1982).
Findlay, John A., et al., Frondogenin, A New Aglycone From the Sea Cucumber Cucumaria Frondosa. *J. Natural Prod.*, 47(2):320–324, Mar.–Apr. (1984).

*Primary Examiner*—Howard C. Lee
*Attorney, Agent, or Firm*—Rothwell, Figg, Ernst & Kurz

[57] ABSTRACT

The invention concerns fractions from echinoderms of the class Holothuroidea (sea cucumber) that can be used directly as active therapeutic agents or as raw materials in producing biologically active derivatives thereof. The fractions can be used alone or in combination and are derived from a) the epithelial layer, free of muscle and collagenous tissues, b) the isolated flower, or c) the whole body wall substantially free muscle, viscera and flower. The invention also concerns processes for obtaining these fractions that involve the use of thermal/mechanical and/or enzymatic means.

18 Claims, 5 Drawing Sheets

PROCESS FOR OBTAINING MEDICALLY ACTIVE FRACTIONS FROM SEA CUCUMBERS

FIELD OF THE INVENTION

The present invention involves the extraction and purification of biologically active materials from tissues of echinoderms of the class Holothuroidea (sea cucumbers).

BACKGROUND OF THE INVENTION

Pharmaceutical companies are expanding efforts to screen and assay biologically active compounds from natural sources. The term that has been applied to this discovery process is "bio-prospecting." When bio-prospecting is successful in finding and identifying promising compounds, efforts are then made to determine and perfect the process by which the compound is produced in its active form. Useful processes develop from these bio-prospecting discoveries, as well as useful compositions of matter and methods of using the same.

The sea cucumbers constitute the taxonomic Class Holothuroidea, Phylum Echinodermata. They possess an elongated body comprising a thick, leathery body wall of epithelial and collagenous layers surrounding the internal organs or viscera, an anterior mouth surrounded by numerous retractile tentacles (herein referred to as the "flower"), and a posterior portion comprising cloaca and anus. Muscle bands are found along the length of the interior surface of the body wall.

Sea cucumbers are a well-known Chinese delicacy harvested from many areas of the world and are a valuable trading resource in Chinese-speaking countries. There are a number of patent applications by Chinese groups relating to sea cucumbers as nutritional supplements (e.g., Chinese application CN 1065019) and patents or applications from Japanese groups relating to various carbohydrate moieties from sea cucumber as anticoagulants (JP 94070085 B2; WO 9008784) and as active components for treating AIDS (WO 9202231; WO 9009181). Historically, sea cucumbers for the worldwide market have been harvested, boiled with the muscles intact, and then salted and dried over an open flame. Salting and drying are the traditional methods of obtaining a product that is safe for storage and transportation. Nutritional supplements have been prepared by finely dividing these salted and fire-dried sea cucumber body walls for use in encapsulated products.

Sea cucumber tissue has been found to contain numerous compounds having potential as biologically active agents in medical and veterinary applications. These include sulfated polysaccharides (e.g. fucosylated chondroitin sulfate, Viera & Mourao, *JBC*, vol. 263, pp. 18176–83 (1988)) sterol glycosides, saponins (e.g., frondogenin and its glycosides, Findlay et al., *J. Natural Products*, vol. 47, pp. 320–324 (1984)), lactones (e.g., triterpenoid lactones, their acetates and glycosides, Findlay et al., supra), peptides, protamines, glycogens, saccharides (e.g. fucose, galactosamine, glucuronic acid, quinovose, xylose or O-methylglucose, Findlay et al., supra), polysaccharides (e.g., polyfucose sulfate, WO 9202231) and various amorphous compounds rich in saccharide moieties (Findlay et al., supra).

Given the lack in the art of refined methods for purifying active fractions from sea cucumber tissues, the biological properties of sea cucumber tissues have been poorly characterized and poorly understood, and their potential as sources of biologically active agents has been little-investigated.

SUMMARY OF THE INVENTION

The present invention relates in part to methods by which biologically active fractions of sea cucumber can be extracted, either for further purification or for use in a pre-purified state. The present invention also relates to compositions of matter comprising these biologically active fractions, their active derivatives and combinations thereof. The methods of the present invention produce usable basic therapeutic products, and basic raw materials for further purification of active derivatives.

DETAILED DESCRIPTION OF THE INVENTION

Figure 1A:
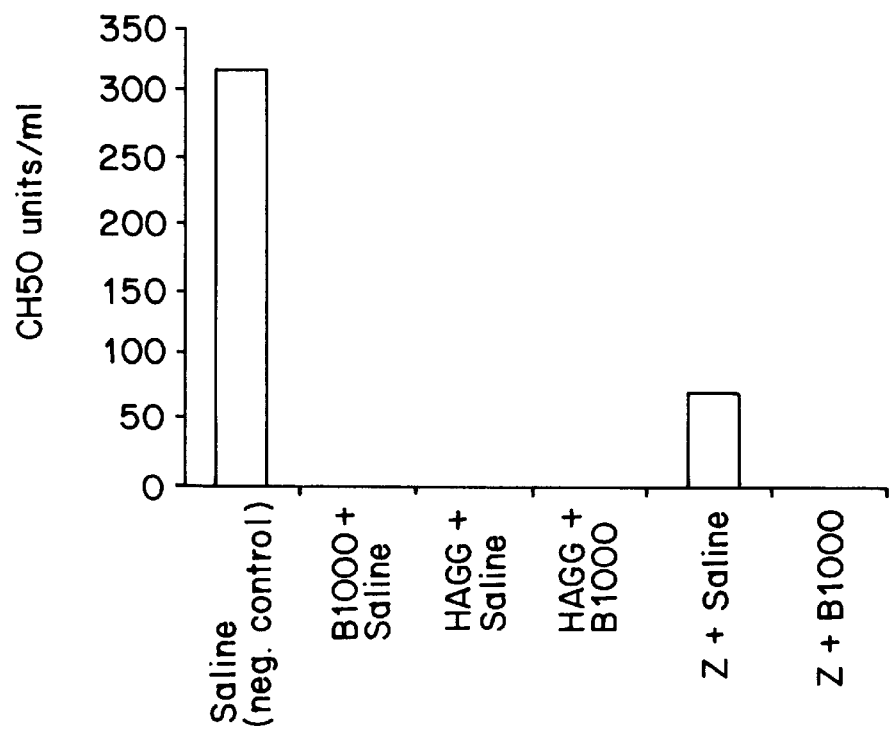
FIGS. 1 A–D—Graphs showing inhibition of classic complement pathway by B1000 according to four different parameters.

The present invention improves upon traditional methods used to process sea cucumbers. Useful fractions according to the present invention can be produced from virtually any species of sea cucumber, such as species of the genera Actinopyga (e.g., *A. lacanora, L. echinites*), Cucumaria (e.g., *C. frondosa, C. echinata, C. chronhjelmi*), Eupentacta (e.g., *E. quinquesemita*), Halodeima (e.g., *H. cinerascens*), Holothuria (e.g., *H. pervicax, H. atra, H. edulis, H. scabra, H. monoacaria, H. leucospilota*), Leptosynapta (e.g., *L. inhaerens*), Ludwigothuria (e.g., *L. grisea*), Microthele (e.g., *M. nobilis*), Molpadia (e.g., *M. musculus*), Parastichopus (e.g., *P. nigripunctatus*), Paracaudina (e.g., *P. chilensis*), Pelagothuria, Pentacta (e.g., *P. australis*), Polycheira (e.g., *P. rufescens*), Psolus (e.g., *P. chitonoides*), Stichopus (e.g., *S. japonicus, S. chloronoyus, S. variegatus*), Synapta (e.g., *S. maculata*), Thelenota (e.g., *T. ananas*) or Thyone (e.g., *T. briareus*). The fractions obtained by the present invention are themselves novel and useful as sources of biologically active agents.

As used herein, the term "sea cucumber" refers to any species of the Phylum Echinodermata, Class Holothuroidea;

the term "flower" refers to the anterior portion of the sea cucumber comprising the mouth and retractile tentacles;

the term "B1000" refers to the isolated epithelial layer of the sea cucumber, substantially free of the flower portion, muscle, collagenous tissues and viscera;

the term "T2000" refers to the isolated flower portion of the sea cucumber, substantially free of other portions of the sea cucumber body;

the term "active derivative" refers to any compound, fraction or combination thereof, derived from a sea cucumber fraction described herein that has biological activity or nutritional properties.

In one embodiment, sea cucumbers are first cleaned of muscle bands and viscera, boiled (but not salted), preferably for about ½ hour, and then dried, preferably in low-heat mechanical driers such as those employing "heat pump" technology. The dried tissue can further be ground or divided as needed for ultimate use. This process decreases the sodium content of the tissue and helps protect various active ingredients from degradation. Processing in this manner produces a dried isolated sea cucumber body-wall that is dramatically different from traditional products obtained by traditional methods, and is suitable for formulation and use directly as a biological agent, either alone or in combination with other sea cucumber fractions or for further purification to obtain active derivatives, or even for use as a food supplement.

In another embodiment of the present invention the flower portion of the sea cucumber is isolated for use. During the evisceration process described above, the anterior portion ("flower") of the sea cucumber is cut away from extraneous viscera and body wall. The isolated flower is then heated, preferably for about ½ hour, dried at low temperatures (e.g. between about 140° F. and about 180° F. using conventional drying apparatus and per se known techniques). This dried fraction, designated "T2000" by the inventor, can then be ground or divided as needed for formulation and use directly, either alone or in combination with other sea cucumber fraction, for use as raw material for purification of active derivatives or even for use as a food supplement. The method and extent of division of the material is not critical to the invention, and can readily determined by those skilled in the art according to the use to which the product will be put.

In still another embodiment of the present invention, the epithelial layer of the sea cucumber body wall is isolated for use. This embodiment involves removal of muscle, viscera and flower, as described above, followed by isolation of the epithelial layer of the sea cucumber body wall from the harder collagenous layers beneath, preferably by one or more of the following means:

heating the body-wall in water at temperatures from about 140° F. to about 180° F., preferably at about 170° F., followed by mechanical separation by hand or machine (e.g., using machines known in the art as mincers or de-boners, which detect tissue density and separate harder tissues from softer tissues);

enzymatic hydrolytic separation, using, e.g., organism's own digestive tract enzymes, proteases from mammalian sources, proteases from non-mammalian sources or acidic hydrolazes, preferably Alcalase (NOVO Nordisk Bio Chem, North Carolina), the enzyme preferably being in a solution of about 1% to about 10% enzyme, most preferably in a solution of about 10% enzyme;

scouring/scrubbing or de-boning processes known to those skilled in the potato or chicken processing arts.

Heating in water, followed by mechanical separation using a de-boner is most preferred.

The epithelial fraction so obtained (designated "B1000" by the inventor) is a dark, moist, viscous, carbohydrate-rich matter. B1000 can be dried as described above and used directly, either alone or in combination with other sea cucumber fractions, in numerous medical applications or used as a raw material for the purification of active derivatives.

The above-described sea cucumber fractions have numerous uses. They can be used alone or in combination as nutritional supplements. They have been found to possess various biological activities, including strong anti-phlogistic and anti-inflammatory activities, serine protease inhibitory activity, anti-complement activity and anti-angiogenic activity. When used as a therapeutic agent, the sea cucumber fractions of the present invention may be in the form of powders, capsules, tablets solutions, suspensions, ointments, or any other means of delivery which those skilled in the medical and veterinary arts would deem appropriate for the intended use. The formulation is dictated by the application, e.g., an application wherein advantage is taken of the compositions' anti-inflammatory properties to treat arthritis in the hands might call for a topical formulation, whereas treatment of a liver malignancy, taking advantage of the compositions' antiangiogenic properties, might call for a formulation suitable for direct injection into the site of malignancy. It is well with the skill of the medical or veterinary arts to determine a suitable formulation for any particular application. Furthermore, methods of making such formulations are well-known in the art (see, e.g. *Remington's Pharmaceutical Sciences,* 18th ed., Mack Publishing Co., Easton, Pa. (1990)). The active ingredient can be administered within a range of from about 0.01 to about 100 w/w %, or more preferably, of from about 0.05 to about 80 w/w %. The dose per day thereof, also depending upon the particular use to which the composition is put, the frequency of administrations, the form of medicament, the symptoms, age and body weight of the recipient of the composition, can be within a range of from about 0.1 to about 1,500 mg of the effective ingredient per kg of body weight, preferably from about 1 to about 1,000 mg/kg, and most preferably about 10 mg/kg. The daily dosage of administration may be divided into two to four separate doses.

As there are a number of combinations of procedures which are effective in producing the above described sea cucumber fractions, the following Examples are meant to illustrate, but in no way to limit, the invention set forth in the claims.

EXAMPLE 1

Preparation of Whole Body Wall from Sea Cucumber

Muscle meat, viscera, anterior and posterior portions of the sea cucumber *Cucumaria frondosa* were removed in order to leave a sea cucumber body wall free of most, if not all of the above named portions. The thus obtained body wall was boiled for about ½ hour in fresh water and dried in a low heat utilizing a 40 hp "heat-pump" dryer (Southwind Mfg., Nova Scotia, Canada). The body wall fraction was dried to about 3% moisture and finely divided.

EXAMPLE 2

Mechanical Extraction and Processing of Sea Cucumber Epithelium

A fraction termed B1000, consisting of sea cucumber epithelium, was produced by the following method. The anterior, posterior, viscera and muscles were removed from sea cucumbers of the species *Cucumaria frondosa* to obtain an isolated body wall. Body wall portions thus obtained were heated for about 30 minutes in fresh 170° F. water, then cooled on wire racks to room temperature. Next, the body wall portions were passed through an industrial machine known to those in the food processing arts as a de-boner or mincer (Paoli Machine, Illinois). The de-boner was adjusted to separate the softer outer epithelial layer from the harder collagenous portion of the body wall. The black viscous layer of the epithelium so separated, designated B1000 by the inventor, was dried by conventional means using a 40 hp "heat pump" dryer as in Example 1 to approximately 3% moisture content and finely divided to obtain a powder.

EXAMPLE 3

Enzymatic Extraction and Processing of Sea Cucumber Epithelium

Enzymes were used to help separate the epithelial layer from the harder collagenous inner layer of body walls from sea cucumbers of the species *Cucumaria frondosa*. The body wall portions were isolated and heated in water as described in Examples 1 and 2. They were then soaked in a solution of 10% Alcalase (NOVO Nordisk Bio Chem, North Carolina) in fresh water at a temperature of 130° F. (±30° F.). The time of soaking depended on the condition of the particular lot of body walls and their characteristics, and varied from about 15 min. to about 3 hours. The average time soaking in the enzyme solution was about one half hour. The body walls were then removed from the enzyme solution and processed by hand to further isolate the black epithelial layer B1000 from the underlying collagenous tissues. The B1000 thus obtained was dried and powdered as in Examples 1 & 2.

EXAMPLE 4

Extraction and Processing of Sea Cucumber Flower

A fraction termed T2000, derived from the sea cucumber flower, was obtained in the following manner.

During the processing operation of removing viscera and muscle set forth in Examples 1 and 2, the anterior portion of the sea cucumber *Cucumaria frondosa* was removed, taking care to include the mouth portion of the head with surrounding tentacles, which is a tissue rich in calcium carbonate (among other compounds). This separated flower portion was then boiled for about ½ hour to obtain the fraction designated T2000 by the inventor. The T2000 was then dried in a conventional "heat-pump" dryer as in Examples 1–3 and finely divided.

EXAMPLE 5

Preparation of Derivative Fractions of B1000 and T2000

The finely divided powders of epithelial layer (B1000) and flower fraction (T2000) obtained in Examples 2 and 4, respectively, were further processed by mixing in an aqueous solution and rotating for 12 hours with a magnetic stirrer. The resultant solution was centrifuged at 30,000 RPM for one hour and the supernatant was removed and lyophilized.

EXAMPLE 6

Antiphlogistic Activity of B1000 and T2000 as Determined by the "Rat Granuloma Pouch Assay"

Method: Roberet, A. and J. E. Nezamis, "The Granuloma Pouch as a Routine Assay for Antiphlogistic Compounds," Acta Endocrinologica: 25, p. 105–112 (1957) (incorporated herein by reference).

Procedure: Thirty-nine Sprague-Dawley male white rats, weighing about 300–350 grams each, were used in the test. They were divided into 7 groups of 5 rats each and 1 group of 4 rats.

The rats were confined to individual cages in the animal room. The temperature was maintained at 23° C.±1° C. The rats had free access to Rodent Teklad Laboratory Diet and fresh water at all times. The rats did not have any disease or exhibit any abnormalities.

The rats were clipped over their dorsal surface with a pair of fine electric clippers. The rats were then anesthetized with Sodium Pentobarbital, given intraperitoneally (0.5 ml equivalent to 3 mg). Using a sterile syringe, 25 ml of air was injected under the skin to produce a pneumoderma. All the pouches were made just over the shoulder blades. This was followed by 0.5 ml of a sterile 1% solution of croton oil made up in corn oil, injected directly into the pouch.

Samples were prepared by mixing powdered B1000, T2000, or sea cucumber body wall fraction with corn oil. All of the rats were treated for a total of five days with the respective compounds made up on a volume of 0.25 ml. All treatments were given by gavage. Dose was 10 mg/kg body weight.

After five days of treatment, the rats were sacrificed and the volume of exudate was measured with a hypodermic syringe. Scissors were used to open each pouch to be certain that all of the exudate had been removed. Results are summarized in Table I.

TABLE I

Comparison of treatment groups, average pouch exudates and body weight gains. Dose - 10 mg/kg body weight.

| Group | Treatment | No. Rats Per Group | Pouch Exudate (ml) | Mean Body Weight (g) |
|---|---|---|---|---|
| I | Neg. control - water | 5 | 9.48 | +21.2 |
| II | Pos. control - hydrocortisone | 5 | 3.74 | -32.4 |
| III | T2000 | 5 | 2.88 | +12.0 |
| IV | B1000 | 5 | 2.86 | +5.4 |
| V | sea cucumber body wall | 5 | 6.84 | -7.0 |
| VI | sea cucumber body wall | 5 | 4.18 | -15.0 |
| VII | sea cucumber body wall | 5 | 6.14 | +4.0 |
| VIII | sea cucumber body wall | 4 | 6.70 | +1.0 |

Pouch Exudate: The average pouch exudate varied from 9.48 ml in the water treated group (negative control) to 2.86 ml in the B1000 treated group. T2000 gave an exudate value of 2.88 ml. These were excellent values compared to the positive control, hydrocortisone 3.74 ml). In fact, they were better than 10 mg/kg of hydrocortisone but without the weight loss seen in the hydrocortisone treated group.

The other sea cucumber preparations had average pouch exudate values 4.18–6.84 ml per rat. These were better values than the negative control of 9.48 ml. It is difficult to correlate the weight loss or low weight gain with the anti-inflammatory activity.

Body Weights: Body weight gain ranged from 21.2 for the negative control to a weight loss of 32.4 g. per rat in the hydrocortisone treated group.

The T2000 group and the B1000 group had weight gains of 12 grams and 5.4 grams, respectively. Both these groups showed excellent anti-inflammatory response. Groups treated with sea cucumber body wall had both weight gains and weight losses.

It appears that the anti-inflammatory effect is unrelated to the weight loss in the sea cucumber products in the treated groups, sea cucumber products. There must be other growth inhibition present.

Summary: The rat granuloma pouch test for anti-inflammatory activity of various sea cucumber fractions or extracts, when compared to a negative control (water) and a positive control (hydrocortisone) indicate the following:

1. T2000 and B1000 have an anti-inflammatory activity better than 10 mg. hydrocortisone.
2. The mean exudate for the water control was 9.48 ml and for the hydrocortisone treated group was 3.74 ml.

3. Sea cucumber body wall caused pouch exudate up to 4.18 ml, which indicates it is almost as good as 10 mg hydrocortisone per kilogram body weight.

EXAMPLE 7

Anti-inflammation Activity of B1000 as Determined in a Mouse Model of *P. aeruginosa* Infection Inflammation Materials and Methods.

Bacterial strains and preparation of inocula: *P. aeruginosa* 6294 was kept frozen at −85° C. as individual aliquots in trypticase soy broth with 15% glycerol. The bacteria from these frozen stocks were inoculated onto trypticase soy agar overlaid with a 12,000 MW cutoff dialysis membrane. After overnight growth, the bacteria were harvested from the membranes with a sterile cotton swab and suspended in sterile 1% proteose peptone to an optical density at 650 nm of 0.92 to achieve a bacterial concentration of approximately $2 \times 10^9$ cfu/ml. The bacteria were diluted 1:10 sterile 1% proteose peptone to achieve the desired final concentration. The actual bacterial concentration was confirmed by plating of appropriate dilutions, in duplicate, onto Maconkey's agar. The dose of 6294 required to establish infection in 50% of mice challenged with this strain (ID50 value) is $1.93 \times 10^5$ cfu (95% confidence interval; $3.25 \times 10^4 - 16.6 \times 10^5$). Thus, the challenge dose for this experiment is approximately 50 times the ID50 value.

Infection of Mice: C3H/HeN female mice (8 weeks old) were obtained from Charles River Breeding Laboratories, Wilmington, Mass. Groups of 5 mice were given an intraperitoneal injection of 0.2 ml of a cocktail containing 6.7 mg of ketamine hydrochloride (Parke Davis, Morris Plains, N.J.) and 1.3 mg of xylazine (Haver, Shawnee, Kans.) per ml. After the animals were anesthetized, they were placed under a stereoscopic microscope, and three 1-mm-long scratches were made in the corneal epithelium and superficial stroma with a 27-gauge needle. Care was taken not to penetrate the stroma to the anterior eye chamber. The bacteria were immediately inoculated onto the abraded cornea in a 5-μL volume dispensed from a micropipette. The mice usually regained consciousness 15–25 minutes after inoculation. All procedures were in accordance with the Association for Research in Vision and Ophthalmology Resolution on the Use of Animals in Research and were approved by the Harvard Medical Area Standing Committee on Animals.

Grading of corneal infection: Infected eyes were graded every 24 hours after inoculation for a total of six days by an investigator unaware of the treatments that the groups received. The following grading scheme was used: grade 0, eye macroscopically identical to the uninfected contralateral control eye; grade 1, faint opacity partially covering the pupil; grade 2, dense opacity covering the entire anterior segment; grade 4, perforation of the cornea and/or phthisis bulbi (shrinkage of the eyeball following inflammatory disease).

Preparation of derivative fraction of B1000 and administration to mice: Powdered B1000 was dissolved in sterile distilled water at a concentration of 10 g in 100 ml (10%). The sample was mixed by stirring overnight on a magnetic stirrer. The insoluble material was pelletted by centrifugation at 13000×g for 30 min. and the supernatant was harvested and lyophilized. Approximately 1.6 grams of material were recovered after lyophilization.

Treatment of Mice: B1000 derivative was prepared as described above. The lyophilized powder was dissolved in the drinking water at a concentration of 200 μg/ml, sterilized by filtration through a 0.45 μm filter and put in sterilized water bottles. The bottles were given to the mice immediately after infection. The mice were given a fresh preparation of B1000 derivative in new water bottles after 3 days.

Statistical analysis: Mann-Whitney U test for non-parametric data was used to determine the statistical significance of the corneal scores on the given days.

Results: The results of the macroscopic grading of the infected eyes in the treated and untreated groups are shown in Table II.

TABLE II

| Days post infection | corneal scores | corneal scores | Significance |
| --- | --- | --- | --- |
| 1 | 1,1,1,1,1 | 2,2,2,2,2 | p = .009 |
| 2 | 1,1,2,2,2 | 2,3,3,3,3 | p = .0216 |
| 3 | 1,1,3,3,3 | 3,3,3,3,3 | not significance |
| 4 | 1,1,3,3,3 | 3,3,3,3,3 | not significance |
| 5 | 1,1,3,3,3 | 3,3,3,3,3 | not significance |
| 6 | 1,1,3,3,3, | 3,3,3,3,3 | not significance |

These data indicate that a derivative of B1000 significantly reduced inflammation as indicated by the reduced corneal scores on the first two days after infection with $10^7$ cfu per eye with *P. aeruginosa* 6294. After 48 hours, although there was a trend toward reduced inflammation these groups were not significantly different.

EXAMPLE 8

Inhibition of Tissue Plasminogen Activator by B1000

B1000 prepared as in Example 5 was assayed for their ability to inhibit tissue plasminogen activator by performing a zymographic analysis of conditioned medium from C8161 human melanoma Cells treated with 1, 10 and 100 μg B1000/ml Twenty-four hour serum-free conditioned media from the upper wells of the Membrane Invasion Culture System containing C8161 human melanoma cells with and without different concentrations of B1000 (lanes 1–4) were mixed 2 parts to 1 part Laemmli sample buffer minus reductant. Without prior boiling, 35 μl of these samples were loaded onto a 10% polyacrylamide SDS-gel containing 0.1% gelatin plus plasminogen in the resolving gel and no gelatin/plasminogen in the stacking gel. After electrophoreses, the gels were incubated at room temperature in 50 mM Tris-Cl pH 7.5 plus 2.5% Triton X-100 for 30 minutes with gentle shaking, then incubated for 25 hours in 100 mM glycine pH 8.3/10 mM EDTA at 37° C. After staining with Coomassie Brilliant Blue R-250 (0.25%) in 25% isopropanol/10% acetic acid for 30 minutes, the gel was destained in 10% methanol/10% acetic acid until the was remained clear. A diminution in the tissue plasminogen activator (tPA) double was seen at approximately 65 kDa) with increased dosages of B1000.

EXAMPLE 9

Inhibition of Complement by a Derivative of B1000

Preparation of B1000 derivative: B1000 was pulverized with a mortar and pestle and put into a tube containing 0.15M NaCl at a weight to volume ratio of 100 μg/ml. The tube was rotated to mix at room temperature overnight and the following morning it was centrifuged to spin down the undissolved material. The supernatant was removed, and after final filtration through a 0.22 μm filter, the B1000 derivative was put into a sterile tube, capped tightly and stored at 4° C.

The undissolved material was dried and weighted, and about half was found to have gone into solution. Culture of the unfiltered B1000 derivative on blood agar plates yielded several colonies of at least two different bacterial species, which were not further identified.

Experiment with complement inhibition: Blood was collected from a healthy donor and allowed to clot at room temperature for 60 minutes. The serum was removed from the blood clot, and transferred to a clean tube.

Complement activators with known activities were prepared as positive controls. These included heat-aggregated gamma globulin (63° C., 30 minutes) and zymosan. The former (HAGG) is a potent activator of the classical pathway, and also activates the alternative pathway weakly. The latter (Z) consists of boiled and washed bakers' yeast and is a strong activator of the alternative pathway. HAGG was used at 14 mg/ml and Z at 10 mg/ml. These are relatively high doses. The B1000 extract was used straight.

The experiment was done by mixing 8 parts of the normal human serum (NHS) with 2 parts saline, saline plus activator (or B1000 extract), or activator plus B1000 extract. These mixtures were incubated for 30 minutes at 37° C. and the complement was examined by assaying total complement activity (CH50), C4d, Bb and iC3b split products. Results are shown in Table III.

TABLE III

| Incubation mixture | CH50 | C4d | Bb | iC3b |
|---|---|---|---|---|
| NHS + saline (neg control) | 318 | 5.33 | 2.3 | 119.0 |
| NHS + HAGG + saline | 0 | 25.75 | 32.67 | 861.0 |
| NHS + Z + saline | 75 | 6.43 | 57.45 | 585.0 |
| NHS + B1000 + saline | 0 | 4.38 | 17.32 | 115.5 |
| NHS + HAGG + B1000 | 0 | 5.92 | 36.84 | 242.5 |
| NHS + Z + B1000 | 0 | 4.52 | 74.17 | 436.3 |

Figure 1B:
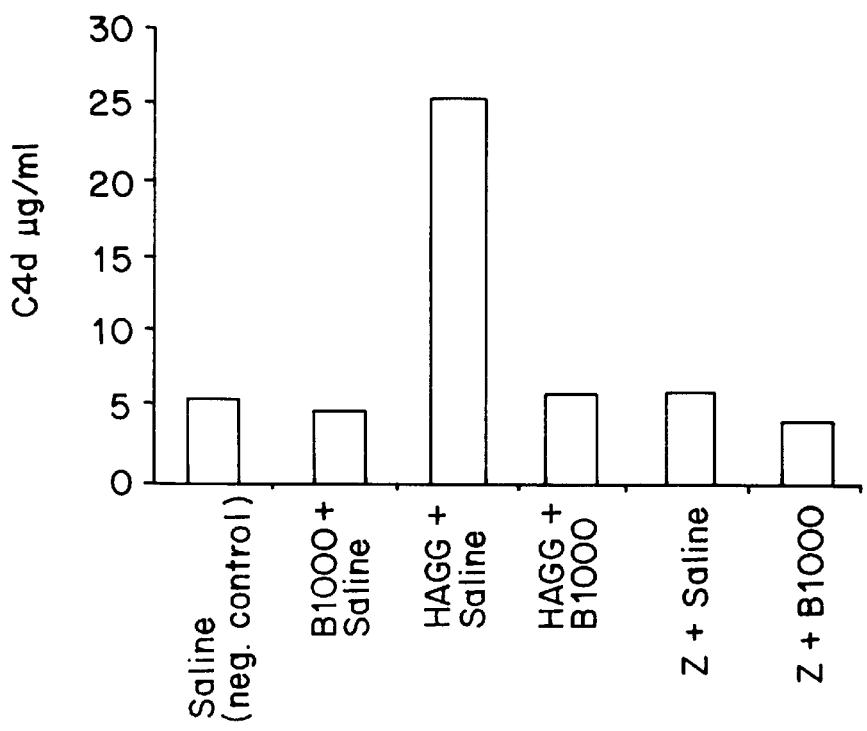
Figure 1C:
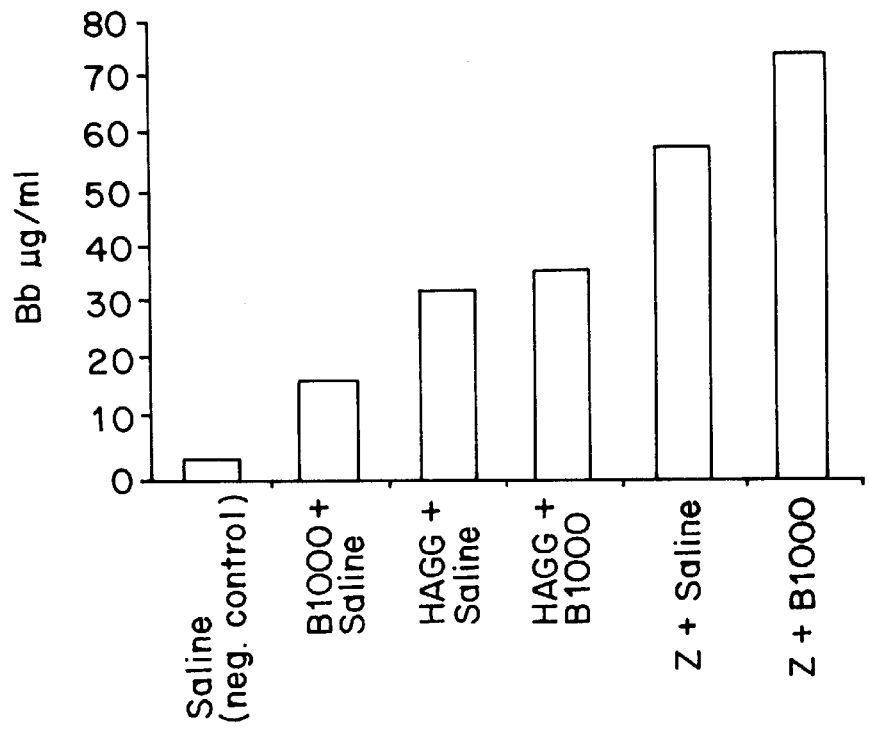
Figure 1D:
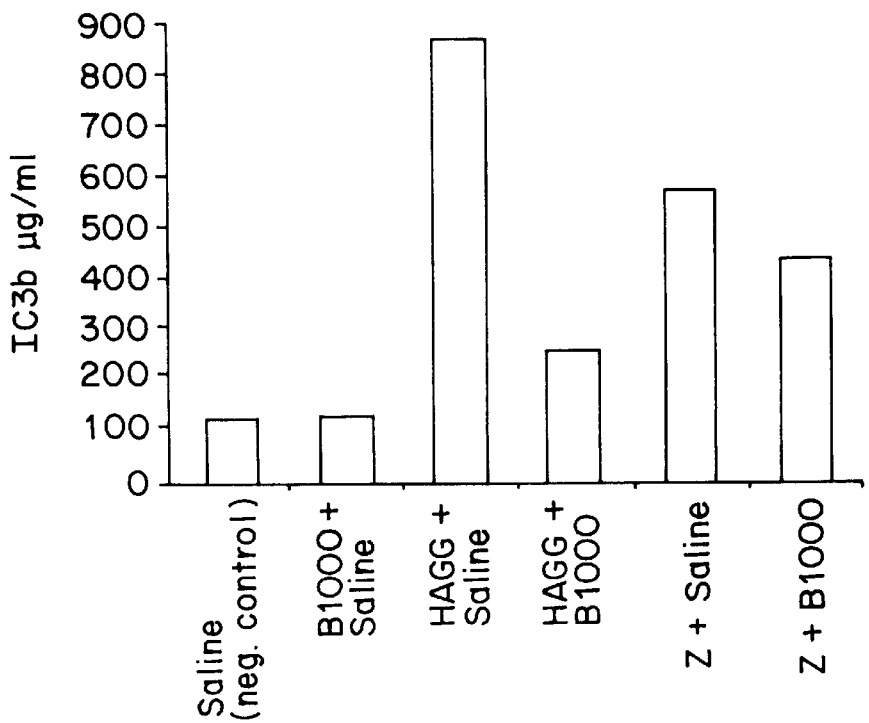

FIGS. 1A–D are graphic representations of the data of Table III. It can be seen in FIG. 1A that the B1000 by itself inhibited the classical pathway activation necessary for CH50 activity. In FIG. 1B, the C4d assay, the HAGG caused a good increase of C4d which it is supposed to do (classical pathway activation) but this increase in C4d was blocked by the B1000. In the Bb assay, there was some activation of the alternative pathway by B1000. This could be due to the polyanions or it could be due to endotoxins released from the contaminating bacteria (which were filtered out, but any soluble products from them would still have been present). There was no decrease in Bb produced by the HAGG or Z, and the increase seen was probably an additive effect of the B1000 activation by itself. In the iC3b assay, it appeared that the B1000 did nothing by itself and that it blocked most of the HAGG-, and some of the Z-mediated iC3b production.

Figure 2:
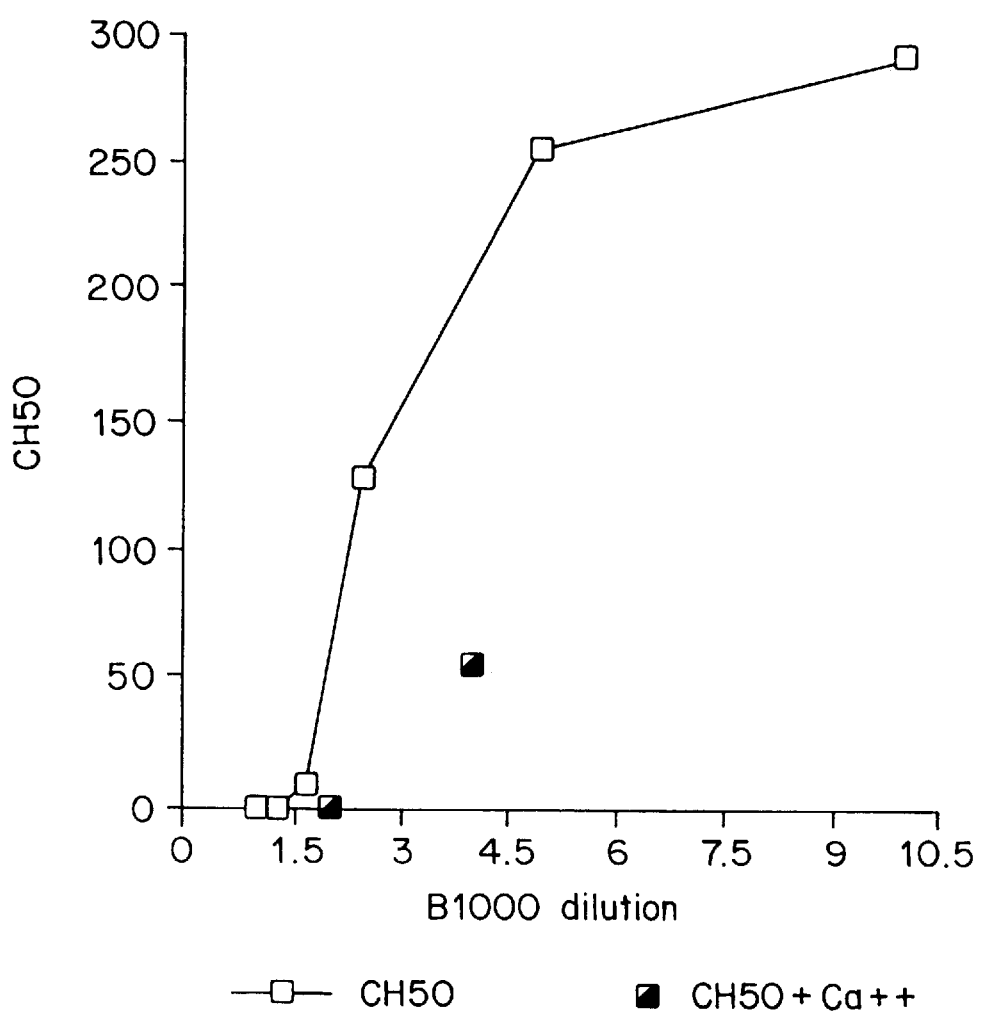
FIG. 2—Effect of B1000 on total complement activity (CH50).

Dose-response of B1000 effect on CH50: In order to find a dose of B1000 that didn't block 100% of the CH50 response (to determine when a slight change is happening in other assays) NHS (as above) was mixed with dilutions of B1000 made in saline. These were incubated at 37° C. for 30 minutes, and then the CH50 assay was done. Results are shown in FIG. 2.

EXAMPLE 10

Nine subjects exhibiting moderately severe to severe arthritic pain were given Ginseng of the Sea™ sea cucumber body wall preparation for periods ranging from 8 to 16 weeks. All patients used a 500 mg capsule supplement orally in the following manner: 3 capsules in the morning and 3 capsules in the evening for 3 weeks, then 2 capsules in the morning and 2 in the evening subsequently. Occasionally, as noted, the patients reduced to 2 capsules per day after the target joint was significantly improved for maintenance supplementation.

A rating scale of 1 to 10, with 1 being very mild and occasional pain which does not limit activity in any way, to 10 which is severe, continuous pain which prevents normal activity, is used as a subjective pain measurement tool in this study.

An 81 year old gentleman presented with left shoulder adhesive capsulitis of one year duration. He rated the pain as a 7 with inability to abduct of forward flex the left shoulder. Dressing was very painful. After 8 weeks supplementation beginning in January, 1996 he rated the pain as a 1 and could fully abduct the shoulder and fully extend the shoulder to a full reach above his head with only minimal pulling feeling. No chiropractic treatments were given to the shoulder.

A 50 year old female presented with cervical spine arthritis of 6 years duration. Radiographs revealed cervical degenerative disc and joint disease at C5, 6 and 7. Pain was rated at 5. She had loss of range of motion. She had been treated for 18 months with temporary resolution of cervical joint pain subsequent to adjustment. Following 12 weeks of supplementation beginning October, 1995 she rated the pain as 2 and had markedly increased ROM of the cervical spine.

A 44 year old male presented with chronic thoracic spine pain of 13 years, status post lifting injury at work. Radiographs revealed degenerative joint disease with loss of disc height and osteophyte formation at T10, 11 and 12. There was hyper-kyphosis at this level. He has been treated once per month for chronic mid-back pain and spasm for 10 years. He rated the pain as 3 after an adjustment but building up to 7 or 8 before the next treatment time. Following supplementation of 12 weeks beginning November, 1995, he rated the pain as a 1 and it only occasionally built prior to adjustment. There was clinically improved intersegmental ROM at the above level and decreased para spinal myospasm which remains stable between treatments for the first time in 10 years.

A 53 year old female presented with cervical spine pain and headache. She had osteoarthritis of the hands with joint enlargement, decreased ROM and mild ulnar deviation. Radiographs revealed cervical spine osteoarthritis. She rated the pain in the cervical spine as 5 and the hands as 7 with inability to knit or do fine work. Following 8 weeks supplementation she had decreased joint enlargement, increased ROM, and rated the pain as a 3 in her hands. Her cervical spine was rated a 3 also. She stated that even her husband has commented on how good her hands look. She had cervical spine manipulation but no hand treatment other than Ginseng of the Sea™.

An 79 year old female presented with severe crippling bilateral hand pain of increasing severity over 1 year. She could only approximate the fingertips to within 3 centimeters of the palm. She had moderate joint edema. She rated the pain as 10. Following supplementation of 8 weeks she began to note improvement. Then in the following 8 weeks she observed significant improvement with improvement of pain and dysfunction. At 18 weeks of supplementation she reported that her pain is 3–4, that she had no swelling in the finger joints, and that all the digits of her right hand touch the palm and all but one of the left fingers could touch the palm.

A 65 year old female presented with chronic knee pain. She rated the pain as a 5 or 6. After six weeks of treatment she reported that the knees are not much improved, but that her chronic arthritis of the proximal interphalangeal joint of the right hand was much better. The edema of the joint was so reduced as to be 50% improved in size with no pain on joint flexion. Following 8 more weeks of supplementation she reported gradual improvement in the knees with pain rating at 3.

A 60 year old male presented with generalized joint discomfort, primarily in the shoulders, neck and upper back. He rated the pain as 4. Following 9 weeks supplementation he rated the pain as 2 and had improved ROM in the involved areas.

A 40 year old male presented with left hip pain. Examination revealed moderate left hip osteoarthritis subsequent to a rollerblading accident 4 years prior. He rated the pain as 5–6 and exacerbating to 8 with increased activity. He also had recurrent left shoulder and neck pain and left knee pain. Following 16 weeks of supplementation beginning in October, 1995 he reported a pain of 1 in his left hip with ability to play basketball without pain. The pain in the left knee was minimal and occasional and there was no left should pain. Remaining cervical spine pain was relieved by cervical manipulation.

A 46 year old male presented with pain the mid-thoracic spine. He had suffered with this pain since an injury in 1975. Thoracic spine films revealed osteoarthritis of T4, 5, 6 with osteophyte formation in this region. He had been using shark cartilage for 2 years with some relief. He was advised to change to the sea cucumber in place of the shark cartilage and within 2 weeks he noted increased motion without pain. Within 8 weeks he noted that the mid-back did not bother with normal daily activity. He mentioned a significant improvement over the shark cartilage.

As can be seen from the forgoing, all patents treated exhibited significant improvement in subjective evaluation of pain and range of movement after treatment.

EXAMPLE 11

Subjective Benefit from Treatment of Arthritic Inflammation with B1000 and T2000

After testing B1000 in a standard LD50 assay ("FHSA/CPSC Design 16 CFR 1500 Acute Oral Toxicity" (Feb. 3, 1995), Tox Monitor of Oak Park, Ill.) to determine existence of toxicity, finely divided B1000, as obtained by Examples 2 and 3, was mixed with sea cucumber collagen and administered in an average dose of 600 mg per day, corresponding to the inhibition of inflammation at 10 mg/kg that was effective in reducing inflammation in laboratory animals, adjusted for patient weight.

Thirty persons were entered into an open label, non-controlled trial to determine presence or absence of subjective benefit in cases of arthritis inflammation and decreased range of motion.

The trial was conducted by Dr. Michael Aker of Blue Hill, Me., and the results are summarized as follows:

Of the 30 patients enrolled in the trial, 28 patients reported subjective benefit as either increased range of motion or lessened pain and inflammation. Twenty-one of those reporting subjective benefit reported that benefit to be an improvement of more than 75% and seven reported improvements at more than 90%.

EXAMPLE 12

Anti-Angiogenesis Using the 10-day Old Chick Embryo Chorioallantoic Membrane Assay (CAM) on Various Sea Cucumber Extracts Method: The conventional method used was as is described D. Knighton, D. Ausprunk, D. Tapper, and J. Folkman, "Avascular and Vascular Phases of Tumor Growth in the Chick Embryo." J. Cancer 35:347–355, 1977.

Procedure: The test compounds were suspended in sterile saline and then applied to methylcellulose discs, ¼" in diameter with a micropipette and allowed to air dry at a concentration of 1 μg/disc. A combination of hydrocortisone and heparin was used as a positive control, as this combination is well known to inhibit angiogenesis.

The test was graded as follows:

0 No change from control embryos

+1 Slight inhibition of vasculature

+2 Moderate inhibition of vasculature

+3 Almost complete inhibition of vasculature

+4 Complete inhibition of vasculature

Results: The CAM Assay antiangiogenesis scores are summarized in Table IV, below. The following scores are averages based on a minimum of 10 eggs used for each sample. All test samples showed antiangiogenic activity. In particular, T2000 was shown to be just as active as the control composition, while B1000 showed an activity greater than the control.

TABLE IV

Antiangiogenic effect of sea cucumber fractions as determined by CAM assay

| Test Sample | Saline Blank (Neg. Ctrl.) | Hydrocortisone/Heparin (Positive Control) | Test sample Results |
| --- | --- | --- | --- |
| sea cucumber body wall | — | 2.8 | 3.5 |
| sea cucumber body wall | 0 | 2.9 | 2.6 |
| sea cucumber body wall | 0 | 3.1 | 2.7 |
| sea cucumber body wall | 0 | 3.4 | 1.8 |
| B1000 | 0 | 3.6 | 3.8 |
| T2000 | 0 | 3.3 | 3.3 |

EXAMPLE 13

Endothelial Tubule Formation (Inhibition of Angiogenesis)

Inhibition of tubule formation was assessed by the methods of Montesano, et al., *J. Cell Biol.*, vol. 97, pp. 1648–1652 (November 1983) (incorporated herein by reference). Endothelial cells (2000) were plated on a tissue culture slide coated with a thin layer of Matrigel according to conventional methods in the presence or absence of test compound. These slides were examined at 18 hours for the presence of tubule formation and graded by two independent observers for the presence of capillary tubules from 0 (no tubules) to 4+ (control tubules). The results are summarized in Table V. All compositions tested showed at least 90% inhibition of tubule formation. B1000 and sea cucumber body wall fraction significantly inhibited tubule formation at concentrations of 0.01% and higher as compared to control ($p<0.05$).

TABLE V

Endothelial tubule formation assay

| Sample | Tubule Formation |
| --- | --- |
| B1000 | 0.005 |
| T2000 | 0.005 |
| sea cucumber body wall | 0.005 |
| sea cucumber body wall | 0.005–0.2 |

EXAMPLE 14

Figure 3:
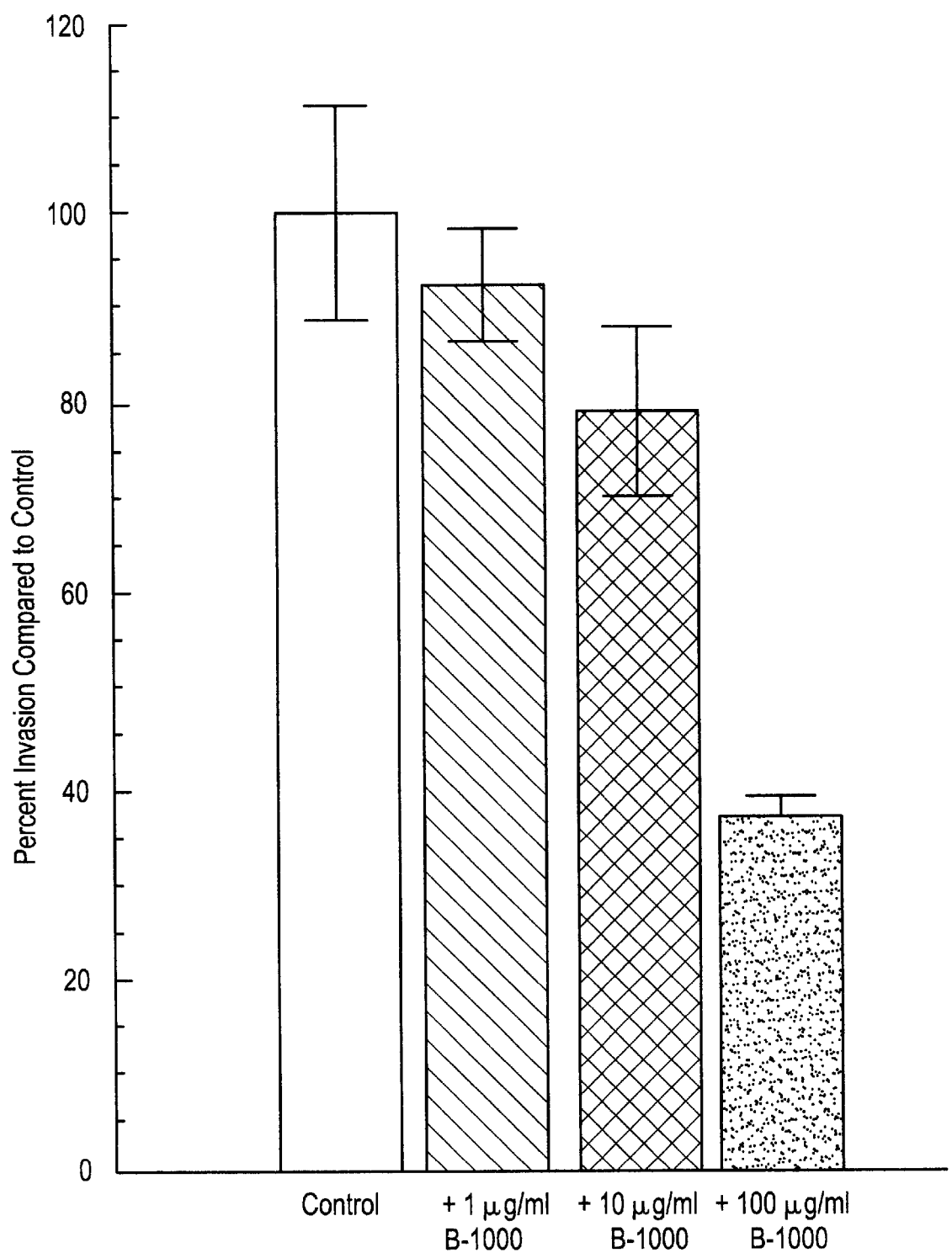
FIG. 3—Effect of B1000 on the invasive potential of C8161 human melanoma cells.

Efficacy of B1000 as an Anti-Invasive Agent Using Human Melanoma Tumor Cell Model Invasion profiles were determined for the human melanoma tumor cell line C8161 using the Membrane Invasion culture System (MICS) assay containing a simple matrix barrier, composed of human basement membrane components (laminin and collagen IV) in a gelatin base (Hendrix et al., *Invasion Metastasis*, vol. 9(5), pp. 278–97 (1989)). Cells were assayed in the presence of 1, 10 and 100 µg B1000/ml for 24 hours, and their ability to invade the basement membrane compared with a control group of untreated cells. The invasive potential of the control group was normalized to 100% and the changes in the treated groups ability to invade calculated as a percent of this value. As seen in FIG. 3, 1 and 10 µg B1000/ml resulted in a slight, though not significant decrease in the invasive potential of C8161; while at 100 µg/ml, B1000 decreased the ability of these cells to invade by the significant value of 63% inhibition.

EXAMPLE 15

Efficacy of B1000 as an Anti-Invasive Agent Using Human Rheumatoid Arthritis Cell Model Rheumatoid arthritis is a disease of the joints which some have likened to a "non-metastasizing" cancerous condition. Like cancer, rheumatoid arthritis is characterized by non-malignant cells becoming hyperproliferative which produces a tissue mass that leads to destruction of tissues. Unlike cancer, rheumatoid arthritis does not have a metastatic component. The destructive and invasive nature of rheumatoid arthritis derived cells was examined. The same three stages associated with this disease which so closely resemble what occurs in cancer were investigated.

Figure 4:
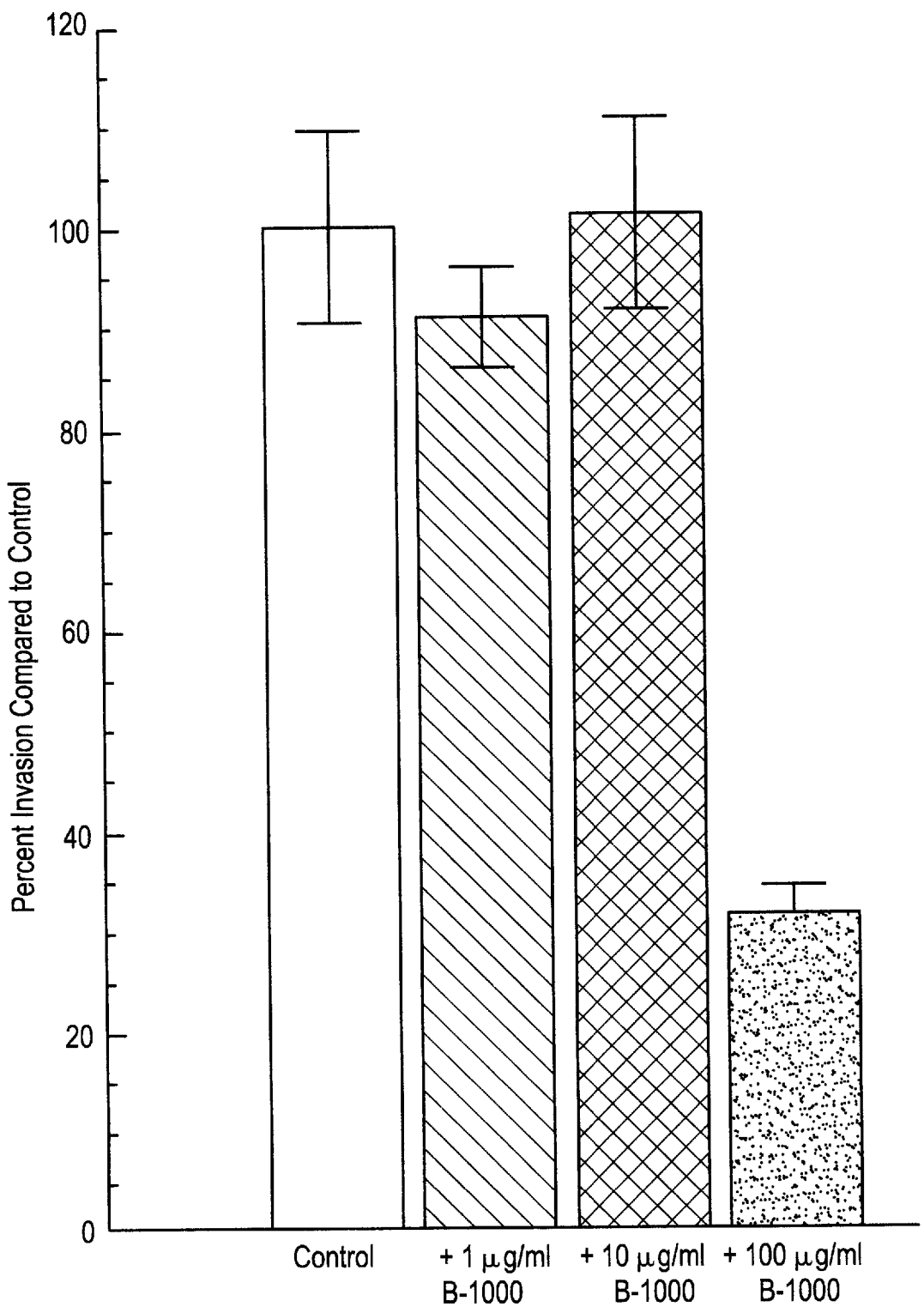
FIG. 4—Effect of B1000 on the invasive potential of RA116 human rheumatoid arthritis cells.

Invasion profiles were determined for the human rheumatoid arthritis synovial fibroblast cell line RA116 using the Membrane Invasion Culture System (MICS) assay containing a cartilage matrix barrier (Hendrix et al., *Invasion Metastasis*, vol. 9(5), pp. 278–97 (1989)). Cells were assayed in the presence of 1, 10 and 100 µg B1000/ml for 48 hours, and their ability to invade compared with a control group of untreated cells. The invasive potential of the control group was normalized to 100% and the changes in the treated groups ability to invade calculated as a percent of this value. As seen in FIG. 4, 1 and 10 µg B1000/ml little-to-no change in the ability of these cells to invade while at 100 µg/ml, B1000 decreased the ability of these cells to invade by the significant value of 69% inhibition.

What is claimed is:

1. A composition comprising the isolated epithelial layer of the sea cucumber, substantially freed of muscle, viscera, flower and collagenous layers.

2. The composition of claim 1 wherein the sea cucumber is of the genus Actinopyga, Cucumaria, Eupentacta, Halodeima, Holothuria, Leptosynapta, Ludwigothuria, Microthele, Molpadia, Parastichopus, Paracaudina, Pelagothuria, Pentacta, Polycheira, Psolus, Stichopus, Synapta, Thelenota, or Thyone.

3. The composition of claim 2 wherein the sea cucumber is of the genus Cucumaria.

4. The composition of claim 3 wherein the sea cucumber is of the species *Cucumaria frondosa*.

5. The composition of claim 1 wherein the epithelial layer is derived from more than one species of sea cucumber.

6. A composition comprising the isolated flower of the sea cucumber.

7. The composition of claim 6 wherein the sea cucumber is of the genus Actinopyga, Cucumaria, Eupentacta, Halodeima, Holothuria, Leptosynapta, Ludwigothuria, Microthele, Molpadia, Parastichopus, Paracaudina, Pelagothuria, Pentacta, Polycheira, Psolus, Stichopus, Synapta, Thelenota, or Thyone.

8. The composition of claim 7 wherein the sea cucumber is of the genus Cucumaria.

9. The composition of claim 8 wherein the sea cucumber is of the species *Cucumaria frondosa*.

10. The composition of claim 6 wherein the mouth parts are derived from more than one genus of sea cucumber.

11. A composition comprising a mixture of isolated sea cucumber epithelial layer, isolated sea cucumber flower and isolated sea cucumber body wall, the isolated sea cucumber body wall being substantially free of muscle, viscera and flower, boiled and dried but not salted.

12. A composition comprising a mixture of isolated sea cucumber epithelial layer and isolated sea cucumber flower.

13. A composition comprising a mixture of isolated sea cucumber epithelial layer and isolated sea cucumber body wall, the isolated sea cucumber body wall being substantially free of muscle, viscera and flower, boiled and dried but not salted.

14. A composition comprising a mixture of isolated sea cucumber flower and isolated sea cucumber body wall, the isolated sea cucumber body wall being substantially free of muscle, viscera and flower boiled and dried but not salted.

15. A method for obtaining active derivatives from the epithelial layer of sea cucumbers comprising the steps of:

(a) removing muscle, (b) removing viscera, (c) removing flower, and (d) removing collagenous layers, wherein said steps can be performed either as individual steps or with two or more of said steps performed simultaneously to yield a product wherein said product is a purified epithelial layer which comprises said active derivatives.

16. The method of claim 15 further comprising the step of drying the separated endothelium.

17. A method for obtaining active derivatives from the sea cucumber flower comprising the steps of:

(a) removing said flower from said sea cucumber to obtain a purified flower and (b) boiling said purified flower, wherein said purified flower comprises said active derivatives.

18. The method of claim 17 further comprising the step of drying the boiled flower.

* * * * *